(12) United States Patent
Medina et al.

(10) Patent No.: US 9,192,574 B2
(45) Date of Patent: *Nov. 24, 2015

(54) CHITOSAN PASTE WOUND DRESSING

(71) Applicant: Medtronic Xomed, Inc., Jacksonville, FL (US)

(72) Inventors: Jennifer Gates Medina, Jacksonville, FL (US); Ethan Glenn Sherman, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/319,901

(22) Filed: Jun. 30, 2014

(65) Prior Publication Data

US 2015/0119358 A1 Apr. 30, 2015

Related U.S. Application Data

(63) Continuation-in-part of application No. 14/061,993, filed on Oct. 24, 2013.

(51) Int. Cl.
| | | |
|---|---|---|
| A01N 43/04 | (2006.01) |
| A61K 9/06 | (2006.01) |
| A61K 31/716 | (2006.01) |
| A61K 31/715 | (2006.01) |
| A61K 31/722 | (2006.01) |
| A61K 47/02 | (2006.01) |
| A61L 27/20 | (2006.01) |
| A61L 27/52 | (2006.01) |
| A61L 24/00 | (2006.01) |
| A61L 24/08 | (2006.01) |
| A61L 26/00 | (2006.01) |

(52) U.S. Cl.
CPC ............... *A61K 9/06* (2013.01); *A61K 31/715* (2013.01); *A61K 31/716* (2013.01); *A61K 31/722* (2013.01); *A61K 47/02* (2013.01); *A61L 24/0031* (2013.01); *A61L 24/08* (2013.01); *A61L 26/008* (2013.01); *A61L 26/0023* (2013.01); *A61L 26/0061* (2013.01); *A61L 26/0071* (2013.01); *A61L 27/20* (2013.01); *A61L 27/52* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 4,394,373 A | 7/1983 | Malette et al. |
| 4,452,785 A | 6/1984 | Malette et al. |
| 4,532,134 A | 7/1985 | Malette et al. |
| 4,572,906 A | 2/1986 | Sparkes et al. |
| 4,659,700 A | 4/1987 | Jackson |
| 4,956,350 A | 9/1990 | Mosbey |
| 5,124,151 A | 6/1992 | Viegas et al. |
| 5,318,780 A | 6/1994 | Viegas et al. |
| 5,623,064 A | 4/1997 | Vournakis et al. |
| 5,688,522 A | 11/1997 | Hardy |
| 5,723,144 A | 3/1998 | Hardy |
| 5,820,608 A | 10/1998 | Luzio et al. |
| 5,871,985 A | 2/1999 | Aebischer et al. |
| 5,902,798 A | 5/1999 | Gouda et al. |
| 5,958,443 A | 9/1999 | Viegas et al. |
| 6,096,018 A | 8/2000 | Luzio et al. |
| 6,344,077 B1 | 2/2002 | Hong |
| 6,344,488 B1 | 2/2002 | Chenite et al. |
| 6,458,375 B1 | 10/2002 | Gertzman et al. |
| RE38,431 E | 2/2004 | Miekka et al. |
| 7,098,194 B2 | 8/2006 | Chenite et al. |
| 7,148,209 B2 | 12/2006 | Hoemann et al. |
| 7,195,675 B2 | 3/2007 | Okazaki et al. |
| 7,307,157 B2 | 12/2007 | Yoshii et al. |
| 7,959,943 B2 | 6/2011 | Hissong et al. |
| 7,968,122 B2 | 6/2011 | Chen |
| 7,976,873 B2 | 7/2011 | Myntti et al. |
| 7,976,875 B2 | 7/2011 | Myntti |
| 8,034,371 B2 | 10/2011 | Castile et al. |
| 8,153,612 B2 | 4/2012 | Ben-Shalom et al. |
| 8,357,787 B2 | 1/2013 | Nichols et al. |
| 8,361,504 B2 | 1/2013 | Hen et al. |
| 8,383,157 B2 | 2/2013 | Muzzarelli et al. |
| 8,389,467 B2 | 3/2013 | Chaput et al. |
| 8,431,160 B2 | 4/2013 | O'Hagan et al. |
| 8,470,346 B2 | 6/2013 | Chen |
| 8,470,369 B2 | 6/2013 | Marchosky |
| 8,506,972 B2 | 8/2013 | Chenite et al. |
| 8,536,230 B2 | 9/2013 | Laurencin et al. |
| 8,653,319 B2 | 2/2014 | Amery et al. |
| 2002/0058704 A1 | 5/2002 | Malik |

(Continued)

FOREIGN PATENT DOCUMENTS

| | | |
|---|---|---|
| EP | 0 329 098 B1 | 5/1994 |
| EP | 1 190 702 A1 | 3/2002 |
| WO | WO 96/13284 | 5/1996 |
| WO | WO 99/07416 | 2/1999 |
| WO | WO 02/40072 | 5/2002 |
| WO | WO 03/020771 A1 | 3/2003 |
| WO | WO 2010/033943 A1 | 3/2010 |
| WO | WO 2011/060545 A1 | 5/2011 |

OTHER PUBLICATIONS

Schaffhausen et al. Abstracts/Journal of Controlled Release (2008), vol. 132, pp. e47-e48.*
Ahmadi et al. Journal of Tissue Engineering and Regenerative Medicine (2010), vol. 4, pp. 309-315.*
Roldo et al., Mucoadhesive thiolated chitosans as platforms for oral controlled drug delivery: synthesis and in vitro evaluation, European Journal of Pharmaceutics and Biopharmaceutics, 57, pp. 115-121 (2004).
Krauland et al., Viscoelastic Properties of a New in situ Gelling Thiolated Chitosan Conjugate, Drug Development and Industrial Pharmacy, 31, pp. 885-893 (2005).

(Continued)

*Primary Examiner* — Patrick Lewis
(74) *Attorney, Agent, or Firm* — IPLM Group, P.A.

(57) ABSTRACT

A method for treating a wound with a ready-to-use composition having a high concentration of a water-soluble chitosan in a phosphate-containing solution. The composition is a paste at room temperature, has a pH of at least 4, adheres to the body tissue or surgical site and has a residence time of at least 1 day.

19 Claims, No Drawings

(56) References Cited

U.S. PATENT DOCUMENTS

| | | | |
|---|---|---|---|
| 2003/0143274 A1* | 7/2003 | Viegas et al. | 424/486 |
| 2005/0042265 A1 | 2/2005 | Guillot et al. | |
| 2005/0136122 A1 | 6/2005 | Sadozai et al. | |
| 2006/0127873 A1 | 6/2006 | Hoemann et al. | |
| 2006/0172000 A1 | 8/2006 | Cullen et al. | |
| 2006/0287278 A1 | 12/2006 | Hu et al. | |
| 2008/0248991 A1 | 10/2008 | Dyer et al. | |
| 2009/0022770 A1 | 1/2009 | Andersson | |
| 2009/0202430 A1 | 8/2009 | Hoemann et al. | |
| 2009/0269417 A1 | 10/2009 | Gonzalez et al. | |
| 2009/0270514 A1 | 10/2009 | Laurencin et al. | |
| 2009/0291911 A1 | 11/2009 | Myntti et al. | |
| 2009/0291912 A1 | 11/2009 | Tijsma et al. | |
| 2010/0172953 A1 | 7/2010 | Larsen et al. | |
| 2010/0316715 A1 | 12/2010 | Andersson | |
| 2011/0040226 A1 | 2/2011 | Amery et al. | |
| 2011/0245757 A1 | 10/2011 | Myntti et al. | |
| 2011/0313056 A1 | 12/2011 | Buschmann et al. | |
| 2012/0052012 A1 | 3/2012 | Chenite et al. | |
| 2012/0329751 A1 | 12/2012 | Baker et al. | |
| 2013/0004474 A1 | 1/2013 | Ouyang et al. | |

OTHER PUBLICATIONS

Bernkop-Schnürch, Thiomers: A new generation of mucoadhesive polymers, Advanced Drug Delivery Reviews, 57, pp. 1569-1582 (2005).

Bernkop-Schnürch et al., Thiomers: Preparation and in vitro evaluation of a mucoadhesive nanoparticulate drug delivery system, International journal of Pharmaceutics, 317, pp. 76-81 (2006).

Kumar, R. M.N.V. et al., Chitosan Chemistry and Pharmaceutical Perspectives, Chem. Rev., 104, pp. 6017-6084 (2004).

Chelladurai S, et al., Design and Evaluation of Bioadhesive in-Situ Nasal Gel of Ketorolac Tromethamine, Chem. Pharm. Bull. 56(11), pp. 1596-1599 (2008).

Bernkop-Schnürch, A. et al., Thiolated polymers-thiomers: synthesis and in vitro evaluation of chitosan-2-iminothiolane conjugates, International Journal of Pharmaceutics, 260, pp. 229-237 (2003).

Ambrose, U. et al., In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds, Antimicrobial Agents and Chemotherapy, vol. 35, No. 9, pp. 1799-1803 (Sep. 1991).

Ahmadi, R. et al., Biocompatibility and gelation of chitosan-glycerol phosphate hydrogels, Journal of Biomedical Materials Research Part A, 10 pages (2007).

Athanasiadis, T. MBBS et al., Effects of a Novel Chitosan Gel on Mucosal Wound Healing Following Endoscopic Sinue Surgery in a Sheep Model of Chronic Rhinosinusitus, The Laryngoscope, 118, 1088-1094 (2008).

Ling L. et al., Biodegradable and injectable in situ cross-linking chitosan-hyaluronic acid based hydrogels for postoperative adhesion prevention, Biomaterials, 35, pp. 3903-3917 (2014).

Aziz M.A. et al., In vitro biocompatibility and cellular interactions of a chitosan/dextran-based hydrogel for postsurgical adhesion prevention, J Biomed Mater Res. Part B, 103B, pp. 332-341 (2014).

Kourelis K. et al., Effectiveness of chitosan-based packing in 35 patients with recalcitrant epistaxis in the context of coagulopathy, Clinical Otolaryngology, 37(4), pp. 305-330 (2012).

Shikani A.H. et al., Endoscopically guided chitosan nasal packing for intractable epistaxis, American Journal of Rhinology & Allergy, 25(1), pp. 61-63 (2011).

Ha et al., A blinded randomized controlled trial evaluating the efficacy of chitosan gel on ostial stenosis following endoscopic sinus surgery, International Forum of Allergy and Rhinology, vol. 3, No. 7, pp. 573-580 (2013).

Rao S.B. et al., Use of chitosan as a biomaterial: studies on its safety and hemostatic potential, Journal of Biomedical Materials Research, vol. 34, pp. 21-28 (1997).

Malette W.G. M.D. et al., Chitosan: A New Hemostatic. Ann Thorac Surg., 36, pp. 55-58 (1983).

Chou T.C. et al., Chitosan enhances platelet adhesion and aggregation, Biochemical and Biophysical Research Communications,302, pp. 480-483 (2003).

Dutkiewicz J.K., Superabsorbent Materials from Shellfish Waste—A Review, J Biomed Mater Res., 63, pp. 373-381(2002).

Brandenberg G. B.S., Chitosan: A New Topical Hemostatic Agent for Diffuse Capillary Bleeding in Brain Tissue, Department of Neurosurgery, Pathology, and Surgery, University of Nebraska Medical Center and Omaha Veterans Administration Medical Center, vol. 15, No. 1, pp. 9-13 (1984).

Hirano S. et al., Wet spun chitosan-collagen fibers, their chemical N-modifications, and blood compatibility, Biomaterials, 21, pp. 997-1003 (2000).

Belman A. M.D. et al., From the Battlefield to the Street—Experience of a Suburban Fire/EMS Agency with Chitosan Dressing, Emergency Medicine & Critical Care Review (2006).

Wedmore I. M.D. et al., A Special Report on the Chitosan-based Hemostatic Dressing: Experience in Current Combat Operations, Journal of Trauma, vol. 60, No. 3, pp. 655-658 (2006).

* cited by examiner

CHITOSAN PASTE WOUND DRESSING

FIELD OF THE INVENTION

This invention relates to polysaccharide-based wound dressings.

BACKGROUND

A wound is an injury to the skin and may for example be a simple abrasion, burn, cut or a purposeful incision such as a surgical wound. Local wound treatments such as wound dressings may be applied to the wound to provide a barrier to micro-organisms and protect the wound from the external environment. Some wound dressings also support or promote wound healing mechanisms.

SUMMARY OF THE INVENTION

Wound dressings that include biodegradable materials are desirable because they may reduce the trauma associated with removal of the wound dressing from a wound surface. Desirably, the wound dressing also has positive therapeutic effects on wound healing.

The present invention provides, in one aspect, a method for treating a wound comprising: applying to a wound a paste composition comprising a water-soluble chitosan or derivative thereof in a phosphate-containing solution, wherein the composition is a paste at room temperature and has a pH of at least 4, a viscosity of about 1 to about 15 Pa·s., and a residence time of at least 1 day.

The present invention provides, in another aspect, a kit for treating a wound, the kit comprising sterile packaging containing a paste composition comprising a water-soluble chitosan or derivative thereof in a phosphate-containing solution, wherein the composition is a paste at room temperature and has a pH of at least 4, a viscosity of about 1 to about 15 Pa·s., and a residence time of at least 1 day; and printed instructions describing the use of the paste and kit for treating wounds.

DETAILED DESCRIPTION

The following detailed description describes certain embodiments and is not to be taken in a limiting sense. All weights, amounts and ratios herein are by weight, unless otherwise specifically noted. The terms shown below have the following meanings:

The term "adhesion" refers to the sticking together of a body structure or prosthetic material to tissue, to the sticking together of tissue to tissue with which it is in intimate contact for an extended period, or to the formation of tissue that connects body structures, prosthetic materials or tissues to one another across a normally open space.

The term "antimicrobial" when used in reference to a substance means that the substance can kill, significantly inhibit or control the growth of microbes, for example bacteria such as *Staphylococcus aureus, Streptococcus epidermis, Pseudomonas aeruginosa* or *Escherichia coli*.

The term "biocompatible" when used in reference to a substance means that the substance presents no significant deleterious or untoward effects upon the body.

The term "biodegradable" when used in reference to a substance means that the substance will degrade or erode in vivo to form smaller chemical or physical species. Such degradation process may be enzymatic, chemical or physical.

The term "chitosan" refers to a polysaccharide polymer containing randomly distributed β-(1-4)-linked D-glucosamine (deacetylated) and optional N-acetyl-D-glucosamine (acetylated) monomer units, and includes chitosan derivatives in which one or more hydroxyl or amine groups of the polymer have been modified to alter the solubility or tissue adhesive characteristics of the derivative.

The term "conformal" when used in reference to a paste applied to tissue or other body structure means that the paste can form a substantially continuous layer over an area to which the paste has been applied.

The term "hemostat" means a device or material which stops blood flow.

The term "osmolality" means the number of osmoles of solute per kilogram of solvent, as measured using a freezing point depression osmometer.

The term "paste" when used in reference to a substance means the substance is a visibly homogenous, nonporous, opaque material having a soft, malleable, spreadable consistency, for example similar to toothpaste. An opaque gel may be a paste. A collection of free flowing dry solid particles, a non-malleable solid, a porous sponge, a translucent gel, a liquid or a sprayable composition would not be a paste.

The term "protective" when used in reference to a paste applied to tissue or other body structure means that the paste may assist in returning an injured, inflamed or surgically repaired tissue surface to a normal state, e.g., through one or more healing mechanisms such as modulation of an inflammatory response, phagocytosis, mucosal remodeling, reciliation or other full or partial restoration of normal function.

The term "residence time" when used in reference to a paste applied to a wound means the time period during which the paste or portion thereof remains in place in vivo under gross observation.

The term "thin" when used in reference to a protective layer atop tissue or other body structure means having an average thickness less than about two millimeters.

The term "tissue adhesive" when used in reference to a substance means that the substance will adhere to the tissue.

The term "tonicity" when used in reference to a cell's response to an external substance refers to the sum of the concentration of solutes having the capacity to exert an osmotic force across a given membrane. Solutes that cannot cross the cell membrane exert an osmotic force. Depending on the solute concentration of the substance in reference to the cell membrane, tonicity may be referred to as "hypertonic", "hypotonic" or "isotonic". "Hypertonic" refers to a substance with a higher solute concentration outside a cell membrane. As such, when the substance contacts the cell membrane, water in the cell will have a tendency to move out of the cell to balance the solute concentration outside the cell membrane. "Hypotonic" refers to substance with a lower solute concentration outside the cell membrane. As such, water from outside the cell will enter into the cell, causing swelling in an attempt to balance the solute concentration inside the cell. "Isotonic" refers to a substance's solute concentration that is the same as the cell to which it comes in contact. As such, it is considered physiological with the cell and hence there is no net flow of water.

The term "viscosity" when used in reference to a substance is the extent to which the substance resists a tendency to flow when subjected to stress. Viscosity may be measured with a cone and plate viscometer that imposes a specific stress on the substance and the resultant stress deformation or resistance is measured according to ASTM F2103-11 (Part 5). The units of viscosity are reported as Pascal-seconds (Pa·s). For the disclosed pastes, the viscosity values are determined and reported after the paste has been sterilized.

The term "wound" means an opening in the skin through which dermal, subdermal or deeper tissue (e.g. subcutaneous fat, muscle, bone or other tissue) is exposed. The wound may be initiated in a variety of ways (e.g., pressure sores from extended bed rest, wounds induced by trauma, cuts, ulcers, burns, surgical incisions and the like).

The disclosed wound dressing or method includes a chitosan paste that includes a high concentration of a water-soluble chitosan (e.g. chitosan salt), in a phosphate-containing solution, the paste having a pH of at least about 4. The disclosed paste desirably has an off white to yellowish coloration, which makes it easy to visualize when applied. The disclosed paste is also desirably provided in a ready-to-use, storage-stable, injectable or extrudable form, requiring no or minimal preparation. Because the paste desirably does not include crosslinkers, it can be stored for extended time periods and desirably does not require mixing or other similar preparation steps before application.

The disclosed paste desirably is biocompatible, biodegradable and has bactericidal and hemostatic properties. The disclosed paste desirably may be used as a topical wound dressing to absorb a substantial amount of wound exudate without undue desiccation of the wound site. The paste also desirably provides antimicrobial activity or wound healing capability or both at the wound site.

The disclosed paste may be used as a wound dressing in a variety of surgical procedures, including neurosurgery, abdominal surgery, cardiovascular surgery, thoracic surgery, head and neck surgery, pelvic surgery, skin, subcutaneous tissue procedures and the like. The paste is also useful in treating ulcers, burns, cuts and the like.

The disclosed paste may be applied as a thin film or other conformal coating in which case the layer may be relatively thin and exposed to air or other nearby gases, and with a substantially uniform thickness throughout the layer. The disclosed paste desirably is applied to at least an extent sufficient to cover healthy or healable tissue in the wound. In some instances it will be desirable to apply the paste within and not merely atop exposed tissue within the wound. The wound dressing desirably acts as a protective paste desirably adhering to tissues (e.g., cartilage or bone) at the treatment site and resists detachment or other disruption until natural degradation or degradation initiated by irrigation or hydrolysis takes place. The wound dressing may be reapplied as often as needed. The residence time or treatment time may be for example from at least 1 day, at least 3 days, at least 5 days, at least 7 days, at least 15 days, up to about 3 weeks, up to about 4 weeks, up to about 45 days or up to about 60 days. The disclosed paste may be used alone or in conjunction with wound coverings that may include bandages, cotton gauze, absorptive pads or the like.

Applying the wound dressing may significantly reduce or prevent bacterial recolonization or reinfection, and may improve healing. The protective paste may provide various therapeutic advantages including but not limited to bacterial adhesion inhibition, anti-infective properties, local immune modulation, tissue protection, reduction or elimination of pain or bleeding, reduction in inflammation, reduction in adhesions to critical anatomy, and the like. These advantages may arise due to a variety of mechanisms including a) killing bacteria, b) inhibiting bacterial colonization, c) inhibiting the adherence of bacteria to tissue, d) reducing tissue morbidity or abscess formation, e) reducing or preventing disease recurrence (for example, specifically reducing the chronic inflammation related to bacterial toxin and extra cellular polysaccharide matrix (viz., biofilm) toxin), f) coating and protecting tissue during healing, such as by maintenance of a moist wound which promotes platelet aggregation, or by closure of a dry wound without excessive scabrous formation, g) hemostasis and h) delivering therapeutic agent(s) to the treatment site.

The disclosed paste may be prepared by mixing or dissolving the initially solid ingredients (e.g., water-soluble chitosan) in a phosphate containing solution (e.g., phosphate buffered saline (PBS)). A paste is formed at room temperature (e.g. about 20° C. to about 25° C.) when the solid ingredients become solubilized.

Water-soluble chitosans, preferably chitosan salts may be used to form the paste. For example, high concentrations of a chitosan salt may be mixed in a phosphate-containing solution (e.g. PBS, glycerol phosphate disodium salt hydrate or any combination thereof) to provide a ready-to use paste. The paste may be opaque because of the high chitosan concentration or after sterilization. Without intending to be bound by theory, the phosphates and chitosan may react via an ionic reaction to help form the paste. Exemplary chitosan concentrations may be from about 3 wt. % to about 20 wt. %, from about 5 wt. % to about 20 wt. %, from about 8 wt. % to about 18 wt. %, from about 10 wt. % to about 18 wt. %, or about 15 wt. % to about 18 wt. % of the total paste weight. The high chitosan concentrations used in the paste result in desirable viscosities and acceptable syringe delivery force. Desired viscosities range from about 1 to about 15 Pa·s. when tested at 25° C. and a shear rate of 221 $s^{-1}$. This shear rate correlates to the approximate average shear rate the substance may experience as it is dispensed through a standard 30 ml BD™ syringe with a LUER LOCK™ connector at a rate of 1 ml/s.

Exemplary unmodified, water-soluble chitosans and their salts (including chloride, citrate, nitrate, lactate, phosphate, and glutamate salts) may be obtained from a variety of commercial sources including sources described in US Patent Application Publication No. 2009/0291911.

Chitosan may also be synthesized by deacetylation of chitin (poly-N-acetyl-D-glucosamine) to eliminate acetyl groups on the nitrogen atom by hydrolysis. The resulting polymer has a plurality of repeating units (e.g., about 30 to about 3000 repeating units, about 60 to about 600 repeating units, or such other amount as may be desired for the chosen end use) some or all of which contain deacetylated amino groups (e.g., about 30 to about 100% or about 60 to about 95% of the total repeating units), with the remaining repeating units (if any) containing acetylated amino groups. The polymer is cationic and may be regarded as being composed from glucosamine monomers.

The chitosan may have a variety of number average molecular weights, e.g., about 5 to about 2000 kDa, about 10 to about 500 kDa, or about 10 to about 100 kDa. The chitosan may for example be an ultralow molecular weight material having a number average molecular weight less than or about 30 kDa, a low molecular weight material having a number average molecular weight of about 30 to about 400 kDa, a medium molecular weight material having a number average molecular weight of about 200 to about 500 kDa or a high molecular weight material having a number average molecular weight greater than about 500 kDa. A low molecular weight chitosan is preferred. The disclosed molecular weights are weights before sterilization of the paste. The chitosan desirably is in dry particulate form, for example, as free-flowing granules whose average particle diameter is less than about 1 mm, less than about 100 µm, about 1 to about 80 µm, or less than 1 µm.

Chitosan derivatives may also be employed, for example derivatives in which one or more hydroxyl or amino groups have been modified for the purpose of altering the solubility or tissue adhesive characteristics of the derivative. Exemplary derivatives include thiolated chitosans, and non-thiolated chitosan derivatives such as acetylated, alkylated or sulfonated chitosans (for example O-alkyl ethers, O-acyl esters, cationized trimethyl chitosans and chitosans modified with polyethylene glycol). Chitosan derivatives may be obtained from a variety of sources. For example, thiolated chitosans may be obtained from ThioMatrix Forschungs Beratungs GmbH and Mucobiomer Biotechnologische Forschungs-und Entwicklungs GmbH or prepared by reaction of chitosan with a suitable thiolated reactant, e.g., as described in Published PCT Application No. WO 03/020771 A1 or in Roldo et al., *Mucoadhesive thiolated chitosans as platforms for oral controlled drug delivery: synthesis and in vitro evaluation*, European Journal of Pharmaceutics and Biopharmaceutics, 57, 115-121 (2004); Krauland et al., *Viscoelastic Properties of a New in situ Gelling Thiolated Chitosan Conjugate*, Drug Development And Industrial Pharmacy, 31, 885-893 (2005); Bernkop-Schnürch, *Thiomers: A new generation of mucoadhesive polymers*, Advanced Drug Delivery Reviews, 57, 1569-1582 (2005); and Bernkop-Schnürch et al., *Thiomers: Preparation and in vitro evaluation of a mucoadhesive nanoparticulate drug delivery system*, International journal of Pharmaceutics, 317, 76-81 (2006).

The paste desirably has a pH appropriate for contacting human tissue, e.g., a pH of at least 4, a near-neutral pH, or a pH less than 10. An acid, base or buffering agent may for example be included to help maintain an appropriate pH. Buffering agents are preferred and phosphate-containing buffers are most preferred. Exemplary buffering agents include mixtures of barbitone sodium, glycinamide, glycine, potassium chloride, potassium phosphate, potassium hydrogen phthalate, sodium acetate, sodium citrate or sodium phosphate with their conjugate acids (for example a mixture of sodium citrate and citric acid).

Exemplary phosphate-containing buffers are derived from phosphoric acid and a base selected from potassium hydroxide, sodium hydroxide, the potassium or sodium salts of phosphoric acid, mixtures thereof and the like. Exemplary phosphate salts include sodium phosphate dibasic and monobasic, potassium phosphate dibasic and monobasic and mixtures thereof. The concentration of phosphoric acid and base or salt in the disclosed buffering agent may be varied to achieve the desired pH.

Exemplary phosphate-containing solutions include phosphate-containing buffers such as PBS. PBS solutions typically include a combination of one or more phosphate salts and one or more chloride salts. Exemplary phosphate salts include disodium phosphate, potassium dihydrogen phosphate or a combination thereof. Exemplary chloride salts include sodium chloride, potassium chloride or a combination thereof. The salts used to prepare the PBS solution are optionally hydrates. An exemplary combination of salts employs disodium phosphate heptahydrate ($Na_2HPO_4$:$7H_2O$) and potassium dihydrogen phosphate ($KH_2PO_4$), in a so-called 1×PBS solution with concentrations of about 0.01M phosphate, about 0.0027M KCl, about 0.137 M NaCl and a pH of 7.4 at 25° C. PBS buffer solutions may be prepared in other strengths such as 2×, 3×, 5×, 10× or any other suitable strength, with 2×, 3× and so on. PBS solution desirably has a pH of about 9 and about 12. Preferably, the PBS solution is a 3× solution having a pH of about 11.

Phosphates may also be provided as salts of glycerol-3-phosphate (GlyPhos) (e.g. as sodium, potassium, calcium or magnesium salts). Stereoisomeric forms of GlyPhos, preferably the racemic, meso, α and β blends or other forms or blends, may also be used. In some embodiments, the phosphate may be provided by a buffering agent (e.g. PBS), by a salt of GlyPhos or both. Preferably, the phosphate-containing solution is a PBS solution, and most preferably is greater than a 1×PBS solution.

Lubricants and wetting agents may also be included to help maintain paste consistency. In addition, lubricants and wetting agents may aid in dispensing the paste into or onto a desired treatment site. Desirably, the paste should be able to be dispensed by an operator from a suitable delivery device (for example a syringe) using a single gloved hand. One preferred class of lubricants and wetting agents includes hydroxy compounds having two or more hydroxyl groups with the presence of 1,2-diol grouping being desirable. Hydroxy compounds having 2-4 carbon atoms have been found to be particularly useful lubricants. Glycerol is especially preferred. Other compounds include ethane-1,2-diol; propane-1,2-diol; butane-1,3-diol and butane-1,4-diol. Mixtures of hydroxy compounds may be employed, especially mixtures of glycerol and one or more diols. Desired amounts of the lubricants and wetting agents may for example be about 1 to about 15 wt. % or about 2 to about 12 wt. % of the total paste weight.

Depending on the osmolality of the paste, a high chitosan concentration may be used. In such cases, the paste's osmolality may exceed 2000 mOsm/kg. In some embodiments, the paste's osmolality may be up to about 3000 mOsm/kg. Such wound dressing may be desirable to provide a dehydrating wound environment. In other wound treatments, it may be desirable that the paste be physiologically compatible with the cells or tissues to which the paste may be applied. In such cases, the paste desirably has an osmolality such that the paste will be considered isotonic or hypertonic to the cells or tissues to which the paste is applied. In these applications, it is preferable that the paste have an osmolality of less than about 2000 mOsm/kg, for example from about 270 to about 1500 mOsm/kg, while still retaining a viscosity of about 1 to about 15 Pa·s.

To maintain or lower the osmolality without significantly altering or reducing the desired viscosity or the paste-like consistency, it was found that one or more osmolality reducing agents may be optionally used. Recommended amounts of the osmolality reducing agent may for example be about 1 to about 20 wt. %, about 1 to about 10 wt. % or about 2 to about 8% wt. of the total paste weight.

Examples of suitable osmolality reducing agents include polysaccharides other than chitosans that are biocompatible and which reduce osmolality in the disclosed paste but which do not crosslink the chitosan. Examples of such polysaccharides include agars, alginates, carrageenans, celluloses, dextrans, galactomannans, glycogens, hyaluronic acids, and starches.

Preferred polysaccharides include hydroxyl functional or alkyl modified celluloses. Exemplary cellulose materials include methylcellulose, ethylcellulose, hydroxybutyl methylcellulose, hydroxyethylcellulose, hydroxypropylcellulose, hydroxypropyl methylcellulose, carboxymethylcellulose, and mixtures thereof. Without intending to be bound by theory, it is believed that the osmolality reducing agent serves as a "salt scavenger" that may help reduce the paste's osmolality and maintain the desired paste-like consistency.

The paste may for example contain chitosan (and an osmolality reducing agent, if employed) in a combined amount representing about 1 to about 20wt. %, about 10 to about 20 wt. % or about 10 to about 15 wt % of the total paste composition. When an osmolality reducing agent is employed, the chitosan and osmolality reducing agent may for example be combined in a ratio of about 10:1 to about 1:20, about 5:1 to about 1:10, or about 3:1 to about 1:5. The chitosan (and the osmolality reducing agent, if employed) are at least partially and desirably fully dissolved in the phosphate-containing solution.

Exemplary therapeutic agents also may be employed in the disclosed paste and include any material suitable for use at the intended treatment site including analgesics, anti-cholinergics, anti-fungal agents, antihistamines, steroidal or non-steroidal anti-inflammatory agents, anti-parasitic agents, antiviral agents, biostatic paste, chemotherapeutic agents, antineoplastic agents, cytokines, hemostatic agents (e.g., thrombin), immunosuppressors, mucolytics, nucleic acids, peptides, proteins, steroids, vasoconstrictors, vitamins, mixtures thereof, and other therapeutic materials that will be known to those skilled in the art. A useful list of such therapeutic agents may also be found, for example, in U.S. Pat. No. 7,959,943.

The disclosed paste desirably is inherently antimicrobial without requiring addition of a separate antimicrobial agent. Antimicrobial activity may be influenced by the proportion of chitosan in the paste. A separate antimicrobial agent may be employed if desired. A useful list of such antimicrobial agents may be found, for example, in U.S. Pat. No. 7,959,943.

Other adjuvants that may be included in the disclosed paste include dyes, pigments or other colorants (e.g., FD & C Red No. 3, FD & C Red No. 20, FD & C Yellow No. 6, FD & C Blue No. 2, D & C Green No. 5, D & C Orange No. 4, D & C Red No. 8, caramel, titanium dioxide, fruit or vegetable colorants such as beet powder or beta-carotene, turmeric, paprika and other materials that will be known to those skilled in the art); indicators; flavoring or sweetening agents including but not limited to anise oil, cherry, cinnamon oil, citrus oil (e.g., lemon, lime or orange oil), cocoa, eucalyptus, herbal aromatics (e.g., clove oil, sage oil or cassia oil), lactose, maltose, menthol, peppermint oil, saccharine, sodium cyclamate, spearmint oil, sorbitol, sucrose, vanillin, wintergreen oil, xylitol and mixtures thereof; antioxidants; antifoam agents; and thixotropes. Where sustained release or delayed release of a therapeutic agent is desirable, a release agent modifier may also be included.

The disclosed paste typically will be placed in suitable sealed packaging (for example, a syringe, a vial, or pouch made of suitable materials, or a kit containing such packaging and optionally contains printed instructions) and subjected to sterilization before being further packaged if need be with printed instructions describing the proper use of the paste or kit in the treatment of wounds. Sterilization methods that do not unduly discolor (e.g. brown), affect the adhesive strength or viscosity or otherwise unduly affect the paste's consistency are desirable. Suitable sterilization methods include steam, ionizing radiation (e.g. gamma radiation and electron beam (E-Beam)). E-Beam sterilization appears to prevent or limit paste discoloration. E-beam sterilization may be performed at reduced temperatures as described in U.S. Pat. No. 8,653,319 B2 (Amery et al). E-beam or gamma sterilization may for example be used at doses in the range of about 12 to about 40 kGy.

The paste desirably is provided as a ready-to-use composition requiring little or no mixing, stirring, hydration or other preparation. The paste desirably has good shelf life as determined by adhesive strength, viscosity and pH, and preferably may be stored for more than 12 months. For example, the paste desirably may be stored for more than 15 months, more than 18 months or up to 24 months while still maintaining a viscosity of about 1 to about 15 Pa·s. If the paste appears to have separated, re-mixing (e.g. back and forth between two syringes) returns the paste to more homogenous consistency. However, the paste preferably does not separate during storage. The paste is desirably stable at temperatures ranging from about 2° C. to about 60° C. In addition, the paste desirably remains a paste after exposure to extreme temperature ranges imposed during ISTA-2A testing (e.g., about −29° C. to about 60° C.).

The disclosed paste also may have desirable tissue adhesion. In other words, the disclosed paste preferably will adhere or stick to the specific body tissue or passageway to which it is applied without having to fully pack the passageway to obtain adequate retention in the passageway. Desirably, the paste has an adhesive strength such that a separation force of about 5 grams to about 80 grams, about 20 to about 50 grams or about 15 to about 30 grams may be required. The separation force may be measured as the force required when using an MTS™ tensile testing machine operated at a rate of 1 min/s to separate two collagen-coated, rubber hemispheres compressed against one another with about a 4.4 Newton (1 pound) force. The rubber hemispheres may be ultra soft Shore OO, 30 durometer black rubber with a diameter of about 5 cm (2 inches) and height of about 2.5 cm (1 inch) and a collagen coating to which about 0.2 to about 0.5 ml of the disclosed paste is desirably applied to the center of the lower hemisphere. Adhesion strength values are reported for sterilized paste. Desirably, the paste has a residence time in the applied passage or structure of at least 1 day, at least 3 days, at least 5 days, or at least 7 days with or without irrigation. The paste may degrade naturally or by irrigation (e.g. saline solution).

The disclosed paste desirably is non-cytotoxic with cytotoxicity scores of 0, 1 or 2 as measured by guidelines of ISO Guideline 10993-5, Biological Evaluation of Medical Devices-Part 5: Tests for in vitro Cytotoxicity. Desirably, the paste may have a cytotoxicity score of 1 or less.

The disclosed paste desirably is substantially collagen-free. Desirably the paste is sufficiently free of collagen (e.g., containing no collagen at all) so as to be saleable worldwide for use without restriction in humans.

The disclosed paste may be used as a part of a multi-step treatment regimen. For example, a series of steps that may be broadly classified as Cleansing/Disrupting, Killing, Protecting/Coating, and Healing may be carried out. The Cleansing/Disrupting step may be carried out by administering a solvating system like those described in U.S. Pat. Nos. 7,976,873 B2 and 7,976,875 B2 and in U.S. Patent Application Publication No. 2011/0245757A1. The Killing step may be carried out by applying a suitable antimicrobial agent to the treatment site. This may for example be accomplished by including an antimicrobial agent in the solvating system, as a separately-applied agent, or in both the solvating system and the separately-applied agent. An antimicrobial agent may also be applied or administered post operatively. The Protecting/Coating step may be carried out by coating at least part of the thus-treated tissue with the disclosed paste. The Healing step may be carried out by allowing the cleansed, protected and sealed tissue surface to undergo a return to a normal state, e.g., through one or more healing mechanisms such as modulation of an inflammatory response, phagocytosis, or full or partial restoration of normal function. The multi-step treatment regimen may include or be followed by a Clearing step in which the disclosed paste is sufficiently biodegradable to disappear from the treatment site in a desired time period, e.g., more than 5 days, or about 7 to 15 days or by irrigation.

The invention is further illustrated in the following non-limiting examples.

EXAMPLE 1

Paste Formulations

A 3×PBS (pH 11-12) solution was prepared by dissolving PBS tablets in water and the pH was adjusted to pH 11-12 using 1N NaOH. Glycerol if used was then added to the PBS solution to form a PBS/Glycerol solution. To either the PBS solution or PBS/Glycerol solution were added varying amounts of dry ingredients, namely a 30-400 kDa molecular weight chitosan or glycerol phosphate disodium salt hydrate solid and mixed at room temperature to form a paste. The paste was then gamma sterilized. All formulations formed a paste and remained paste at room temperature. Table 1 shows the percentage of the ingredients in the total volume of liquid. Table 1 also shows the osmolality, viscosity and adhesion values for each formulation after sterilization.

TABLE 1

| Formulation | Chitosan HCl (%) | Glycerol (%1) | BGly Ph (%) | Osmolality (mOsm/kg) | Sterile Viscosity (Pa·s.) at Shear Rate 221 (1/s) | Average Sterile Adhesion Force (grams) |
| --- | --- | --- | --- | --- | --- | --- |
| 1 | 13 | 0.6 | | 2087 | 1.9 | 26.6 |
| 2 | 17 | 0.6 | | 1730 | 3.2 | 26.4-37.7 |
| 3 | 17 | 0.6 | 6 | 2882 | 4.9 | 38.3 |

EXAMPLE 2

0.6 ml of 10% glycerol and 5.4 ml of 3×PBS solution (pH 11) were mixed in a 10 ml syringe. To this PBS/Glycerol solution was added varying amounts of glycerol phosphate, chitosan HCL and a hydroxypropyl cellulose (HPC) in solid form. After all the ingredients in the syringe were fully mixed at room temperature, the resultant paste was gamma or E-beam sterilized. The formulations are shown below in Table 2. All the formulations formed a paste at room temperature and remained a paste at room temperature. Table 2 shows the percentage of the various ingredients reported as a percentage of the total volume of liquid. The osmolality, viscosity and adhesion values for each formulation are shown below in Table 3 and are values after sterilization.

TABLE 2

| Formulation | Chitosan HCL (%) | HPC (%) | Glycerol Phosphate (%) |
| --- | --- | --- | --- |
| 4 | 8.5 | 3 | 1 |
| 5 | 13 | 4 | 2 |
| 6 | 10 | 3 | 1 |
| 7 | 10 | 3 | 1.5 |
| 8 | 13 | 2 | 2 |

TABLE 3

| Form-ulation | Osmolality (mOsm/kg) | Sterile Viscosity (Pa·s.) at Shear Rate 221 (1/s) Gamma | Sterile Viscosity (Pa·s.) at Shear Rate 221 (1/s) E-Beam | Sterile Adhesion Force (grams) Gamma | Sterile Adhesion Force (grams) E-Beam |
| --- | --- | --- | --- | --- | --- |
| 4 | Less than 1492 | 3 | 3.2 | 13.5 | 40.6 |
| 5 | Greater than or equal to 1492 | 1.7 | 0.4 | 14.5 | 45.5 |
| 6 | 525 | 1.8 | 2.3 | 22.8 | 65.0 |
| 7 | Less than 1492 | 1.6 | 1.4 | 17.4 | 67.3 |
| 8 | Greater than or equal to 1492 | 2.2 | 3.2 | 19.8 | 50.5 |

EXAMPLE 3

Antimicrobial Properties

Formulations 14, 15 and 16 from Table 2 were evaluated to determine their antimicrobial activity against four common bacterial strains (*S. aureus, S. epidermis, E. coli* and *P. aeruginosa* using a zone of inhibition screening technique.

The four bacteria were grown on Muller Hinton agar plates. Under sterile conditions, approximately 0.1 to 0.2 ml of each formulation was directly placed on the agar plates. The agar plates were incubated at 35° C. for 12 hours. After incubation, the plates were observed for bacterial growth. The use of the term "zone of inhibition" denotes an area around the formulations where bacterial growth was inhibited. The term "bacteriostatic" denotes that the bacteria grew to the edge of the formulation but no further growth was observed. In other words, the term "bacteriostatic" refers to an ability to prevent bacteria from growing and multiplying but possibly not killing them.

The results shown in Table 4 below are based on triplicates per formulation.

TABLE 4

| Bacterial Strains | Zone of Inhibition or Bacteriostatic | | |
| --- | --- | --- | --- |
| | Formulation 4 | Formulation 5 | Formulation 6 |
| S. aureus | zone of inhibition | zone of inhibition | zone of inhibition |
| S. epidermis | zone of inhibition | zone of inhibition | zone of inhibition |
| E. coli | zone of inhibition | zone of inhibition | zone of inhibition |
| P. aeruginosa | bacteriostatic | bacteriostatic | bacteriostatic |

The results show that the formulations were antimicrobial and produced zones of inhibition.

EXAMPLE 4

Cytotoxicity

Formulations 4 and 6 were either E-beam or gamma sterilized and were evaluated for potential cytotoxic effects following the guidelines of ISO 10993-5, Bilogical Evaluation of Medical Devices-Part 5: Tests for in vitro Cytotoxicity. Formulations 4 and 6 were extracted in purified water (PW) at 37° C. for 24 hours. The PW extract was mixed with double strength Minimum Essential Medium (2×MEM) to a 50% concentration. A negative control (high density polyethylene) and reagent control (e.g. PW) were similarly prepared. A positive control (powder-free latex gloves which include natural rubber latex, zinc carbamate accelerators, zinc oxide and titanium dioxide) was extracted in single strength MEM (1×MEM) at 37° C. for 24 hours. Triplicates of a mammalian cell culture monolayer having L-929 mouse fibroblast cells were dosed with each extract (formulations 14, 16, positive, negative and reagent controls) and incubated at 37° C. in the presence of 5% $CO_2$ for 48 hours. Following incubation, the monolayers were examined microscopically (100×) for abnormal cell morphology and cellular degeneration.

To confirm the scores, 0.2 ml of trypan blue stain was added to wells containing the test samples. The trypan blue molecule is large and cannot readily be absorbed by live cells. Only dead cells or those with compromised cell membranes take up the blue colored stain. Table 5 describes the scoring and visual characteristics.

TABLE 5

| Grade/Score | Reactivity | Conditions of all Cultures |
|---|---|---|
| 0 | None | Discrete intracytoplasmic granules, no cell lysis, no reduction of cell growth. |
| 1 | Slight | Not more than 20% of the cells are round, loosely attached and without intracytoplasmic granules, or show changes in morphology; occasional lysed cells are present; only slight growth inhibition observable. |
| 2 | Mild | Not more than 50% of the cells are round, devoid of intracytoplasmic granules; no extensive cell lysis; not more than 50% growth inhibition observable. |
| 3 | Moderate | Not more than 70% of the cell layers contain rounded cells or are lysed; cell layers not completely destroyed, but more than 50% growth inhibition observed. |
| 4 | Severe | Nearly complete or complete destruction of the cell layers. |

Below are the results for Formulations 4 and 6 that were either E-beam (e) or gamma (g) sterilized. The subscript e or g is used to denote the sterilization method.

TABLE 6

| Samples | Percent Rounding | Percent Cells Without Intracytoplasmic Granules | Percent Lysis | Grade | Reactivity |
|---|---|---|---|---|---|
| Formulation $4_e$ | 0 | 0 | 0 | 0 | None |
| Formulation $4_g$ | 0 | 0 | 0 | 0 | None |
| Formulation $6_e$ | 10 | 10 | 10 | 1 | Slight |
| Formulation $6_g$ | 0 | 0 | 0 | 0 | None |
| Negative Control | 0 | 0 | 0 | 0 | None |
| Reagent Control | 0 | 0 | 0 | 0 | None |
| Positive Control | Not Applicable | Not Applicable | 100 | 4 | Severe |

Formulation $6_e$ showed slight cell lysis or toxicity but is generally considered to be non-cytotoxic with a cytotoxicity score of 1. Formulations $6_g$, $4_e$ and $4_g$ were shown to be nontoxic each having a cytotoxicity score of 0.

Some additional non-limiting embodiments are provided below to further exemplify the present invention.

1. A paste in sterile packaging comprising a paste composition comprising a water-soluble chitosan or derivative thereof and a lubricating or wetting agent in a phosphate-containing solution wherein the composition is a paste at room temperature and has a pH of at least 4, a viscosity of about 1 to about 15 Pa·s., and the paste adheres to a surgical site and has a residence time of at least 1 day.
2. A wound dressing comprising a paste composition comprising a water-soluble chitosan or derivative thereof and a lubricating or wetting agent in a phosphate-containing solution wherein the composition is a paste at room temperature and has a pH of at least 4, a viscosity of about 1 to about 15 Pa·s., and the paste adheres to a surgical site and has a residence time of at least 1 day.
3. The embodiment 1 and 2 wherein the water-soluble chitosan comprises a salt.
4. The embodiment 1-3 wherein the water-soluble chitosan comprises a hydrochloric acid salt.
5. The embodiment 1-4 wherein the water-soluble chitosan is about 3 wt. % to about 20 wt. % of total paste weight.
6. The embodiment 1-5 wherein the water-soluble chitosan is about 15 wt. % to about 18 wt. % of total paste weight.
7. The embodiment 1-6 wherein the phosphate-containing solution is a phosphate buffered saline (PBS).
8. The embodiment 1-7 wherein the phosphate-containing solution has a pH of 9 to 12.
9. The embodiment 1-8 wherein the lubricating or wetting agent comprises glycerol.
10. The embodiment 1-9 having a pH of 4 to 7.
11. The embodiment 1-10 wherein the residence time is at least 3 days.
12. The embodiment 1-11 having an adhesive strength of about 5 grams and about 80 grams of force required when using a tensile testing machine operated at a rate of 1 mm/s to separate two collagen coated hemispheres to which the paste has been applied and the hemispheres compressed against one another with a 4.4 Newton force.
13. The embodiment 1-12 that is non-cytotoxic.
14. The embodiment 13 having a cytotoxicity score of 1 or less.
15. The embodiment 1 wherein the sterile packaging is electron-beam or gamma sterilized.
16. The embodiment 15 wherein the sterilization energy is about 12 to about 40 kGy.
17. A wound dressing formed from the embodiment 1.
18. The embodiment 1-2 further comprising glycerol phosphate.
19. The embodiment 1-2 further comprising an osmolality reducing agent.
20. The embodiment 19 wherein the osmolality reducing agent comprises an alkyl or hydroxyl functional cellulose.
21. The embodiment 20 wherein the alkyl or hydroxyl functional cellulose is hydroxypropyl cellulose, methyl cellulose or hydroxyethyl cellulose.
22. The embodiment 19, 20 or 21 wherein the osmolality is about 270 to about 2000 mOsm/kg.

All patents, patent applications and literature cited in the specification are hereby incorporated by reference in their entirety. In the case of any inconsistencies, the present disclosure, including any definitions therein will prevail. Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

We claim:

1. A method for treating a wound comprising:
applying to a wound a paste composition comprising a water-soluble chitosan or derivative thereof in a phosphate-containing solution, wherein the composition is an opaque paste at room temperature containing at least five wt. % of the water-soluble chitosan or derivative thereof based on the total paste weight and having a pH of at least 4, a viscosity of about 1 to about 15 Pa·s., and a residence time of at least 1 day.

2. The method according to claim 1 wherein the water-soluble chitosan comprises a hydrochloric acid salt.

3. The method according to claim 1 wherein the water-soluble chitosan or derivative thereof is up to about 20 wt. % of the total paste weight.

4. The method according to claim 1 wherein the water-soluble chitosan or derivative thereof is about 15 wt. % to about 18 wt. % of the total paste weight.

5. The method according to claim 1 wherein the water-soluble chitosan or derivative thereof has a number average molecular weight of about 5 to about 2000 kDa.

6. The method according to claim 1 wherein the water-soluble chitosan or derivative thereof has a number average molecular weight of about 30 to about 400 kDa.

7. The method according to claim 1 wherein the phosphate-containing solution is a phosphate buffered saline.

8. The method according to claim 1 wherein the phosphate-containing solution is a 3× phosphate buffered saline.

9. The method according to claim 1 wherein the phosphate-containing solution has a pH of 9-12.

10. The method according to claim 1 wherein the phosphate-containing solution comprises a glycerol phosphate.

11. The method according to claim 1 wherein the paste further comprises a lubricant or wetting agent.

12. The method according to claim 11 wherein the lubricant or wetting agent is glycerol.

13. The method according to claim 11 wherein the lubricant or wetting agent is about 1 wt. % to about 10 wt. % of the total paste weight.

14. The method according to claim 1 wherein the paste is sterilized.

15. The method according to claim 14 wherein the sterilization is electron-beam radiation or gamma radiation.

16. The method according to claim 1 wherein the paste has an adhesive strength of about 5 grams to about 80 grams of force required when using a tensile testing machine operated at a rate of 1 mm/s to separate two collagen coated hemispheres to which the paste has been applied and the hemispheres compressed against one another with a 4.4 Newton force.

17. The method according to claim 1 wherein the paste is a non-cytotoxic with a cytotoxicity score of 1 or less.

18. The method according to claim 1 wherein the paste is packaged as a ready-to-use composition.

19. A kit for treating a wound, the kit comprising sterile packaging containing a paste composition comprising a water-soluble chitosan or derivative thereof in a phosphate-containing solution, wherein the composition is an opaque paste at room temperature containing at least five wt. % of the water-soluble chitosan or derivative thereof based on the total paste weight and having a pH of at least 4, a viscosity of about 1 to about 15 Pa·s., and a residence time of at least 1 day; and printed instructions describing the use of the paste and kit for treating wounds.

* * * * *